US00PP33839P2

(12) United States Plant Patent
Gyotoku

(10) Patent No.: US PP33,839 P2
(45) Date of Patent: Jan. 11, 2022

(54) ***THUJA* PLANT NAMED 'QUETHUCOR'**

(50) Latin Name: *Thuja orientalis*
Varietal Denomination: Quethucor

(71) Applicant: Shigemori Gyotoku, Asakura (JP)

(72) Inventor: Shigemori Gyotoku, Asakura (JP)

( * ) Notice: Subject to any disclaimer, the term of this patent is extended or adjusted under 35 U.S.C. 154(b) by 0 days.

(21) Appl. No.: 17/137,460

(22) Filed: Dec. 30, 2020

(51) Int. Cl.
*A01H 5/12* (2018.01)
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

(56) References Cited

PUBLICATIONS

JC Raulston Arboretum, NC State University, https://jcra.ncsu.edu/resources/photographs/details.php?serial=684434, image taken Jun. 2, 2018.*

* cited by examiner

*Primary Examiner* — Anne Marie Grunberg
(74) *Attorney, Agent, or Firm* — Panitch Schwarze Belisario & Nadel LLP; Stephany G. Small; Travis W. Bliss

(57) ABSTRACT

A new and distinct variety of *Thuja* plant, referred to by its cultivar name, 'Coral Queen', is disclosed. The new variety forms attractive bright golden colored foliage turning to bright red in the fall and winter. Slow growing and compact growth habit is provided. The new variety is well suited for providing attractive ornamentation in the landscape.

1 Drawing Sheet

Botanical/commercial classification:
Latin name: *Thuja orientalis.*
Varietal denomination: 'Quethucor'.

SUMMARY OF THE INVENTION

The new variety of *Thuja orientalis* plant originated in a controlled breeding program in Fukuoka, Japan during 1998. The new cultivar was created by cross-pollination wherein two parents were crossed which previously had been studied in the hope that they would contribute the desired characteristics. The female parent (i.e., the seed parent) was the 'H202' variety (non-patented), which is a breeder seedling. The male parent (i.e, the pollen parent) was the 'H110' variety (non-patented), which is a breeder seedling.

The parentage of the new variety can be summarized as follows:

'H202' x 'H110'

The new cultivar was discovered and selected as a single flowering plant from the progeny resulting from the above stated cross-pollination during 2000 in a controlled environment in Fukuoka, Japan. Selective study resulted in the identification of a single plant of the new variety.

It was found that the new variety of *Thuja* plant of the present invention:

(a) forms bright golden foliage color turning to bright red in fall and winter, and (b) provides slow growing and compact growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. In particular, the new variety is more compact and shorter than both 'H202' (i.e., the female parent) and 'H110' (i.e., the male parent). Moreover, the new variety can also be distinguished from other similar varieties that are commercially available. For instance, the new variety of the present invention can readily be distinguished from the 'Aurea Nana' variety (non-patented), as the new cultivar displays a brighter foliage color and a foliage color that fades less compared to the 'Aurea Nana' variety.

The new variety has been found to undergo asexual propagation by softwood cuttings. Asexual propagation by softwood cuttings in Fukuoka, Japan since 2002 has shown that the characteristics of the new variety are stable and are strictly transmissible by such asexual propagation from one generation to another. Accordingly, the new variety undergoes asexual propagation in a true-to-type manner.

The new variety has been named 'Quethucor'.

The first sale of the new variety was on Oct. 1, 2020 by the inventor or by another who obtained the new variety directly or indirectly from the inventor.

BRIEF DESCRIPTION OF THE PHOTOGRAPH

The accompanying photograph shows as nearly true as it is reasonably possible to make the same, in a color illustration of this character, a typical specimen of the plant and plant parts of the new variety. Colors in the photograph may differ slightly from the color values cited in the detailed description, which accurately describes the colors of the 'Quethucor' variety. The plant was approximately four years old and was grown in the ground in November 2015 at Cochranville, Pa.

Drawing—illustrates a specimen of the plant displaying the overall growth and flowering habit—side view.

DETAILED BOTANICAL DESCRIPTION

The chart used in the identification of the colors is that of The Royal Horticultural Society (R.H.S. Colour Chart), 1966 edition, London, England, except where general color terms of ordinary significance are used. The terminology which precedes reference to the chart has been added to indicate the corresponding color in more common terms. The following description is based upon the observation of typical plants of the new variety at an age of approximately two years during the month of February while growing in a container in Cochranville, Pa., U.S.A. The growing conditions approximated those employed for the commercial production of *Thuja* plants.

Propagation:

*Type cutting*.—Semi-hardwood cuttings.

Plant:

*Growth habit*.—Slow growing, compact, perennial evergreen shrub.

*Time to initiate roots*.—6-8 weeks.

*Time to produce a rooted cutting*.—10-12 weeks.

*Commercial crop time*.—18-24 months.

*Resistance to disease*.—No disease susceptibility noticed to date.

*Resistance to pests*.—No pest problems noticed to date.

*General description*.—Height in a one-quart container: 40.0 cm. Width in a one-quart container: 14.0 cm.

*Cold hardiness*.—U.S.D.A. Zones 6 to 9.

*Root description*.—Fibrous.

*Growth rate*.—Slow.

*Stem shape*.—Oval.

*Stem size*.—Main branch: Average of 6.0 mm in diameter and 29.0 cm in length. Lateral branches: Average of 3.0 mm in diameter and 8.0 cm in length.

*Stem surface*.—Young branches are glabrous and knobby with scales.

*Branching*.—Main stem arises from base with numerous secondary branches, number of lateral branches, 8.0 cm in length, an average of 5 per main stem.

*Branch arrangement*.—Alternate.

*Branch aspect*.—Main stems upright, lateral stems held at about an average of 20-30-degree angle from the main stem with flat sprays that spread outwards.

*Internode length*.—1.0 cm.

*Stem color*.—Young stems: commonly near Greyed-Orange Group 174B. Mature stems: commonly near Greyed-Orange Group 177B.

*Flowers, cones, and seeds*.—None observed to date.

Foliage:

*Leaf arrangement*.—Numerous leaves arranged on planar branchlets (closely alternate or opposite), scale-like decussate.

*Leaf shape*.—Facial pair keeled, flat pair flattened and oblong.

*Leaf division*.—Simple.

*Leaf base*.—Cuneate.

*Leaf apex*.—Apiculate.

*Leaf venation*.—Not visible.

*Leaf glands*.—Inconspicuous.

*Leaf margins*.—Entire.

*Leaf surface*.—Upper and lower; glabrous, smooth.

*Winter leaf color of young foliage*.—Upper surface: commonly near Greyed-Orange Group 173B. Lower surface: commonly near Greyed-Orange Group 173A.

*Winter leaf color mature foliage*.—Upper surface: commonly near Greyed-Orange Group 171B. Lower surface: commonly near Yellow-Green Group 146B.

*Leaf size*.—Average of 3.0 mm in length and 1.5 mm in width.

*Leaf quantity*.—About 17 leaves per lateral branch.

*Fragrance*.—Somewhat acrid when crushed.

The new 'Quethucor' variety has not been observed under all possible environmental conditions to date. Accordingly, it is possible that the phenotypic expression may vary somewhat with changes in light intensity and duration, cultural practices, and other environmental conditions, without variance of the genotype.

I claim:

1. A new and distinct cultivar of *Thuja* plant characterized by the following combination of characteristics:

(a) forms bright golden foliage color turning to bright red in fall and winter, and (b) provides slow growing and compact growth habit; substantially as herein shown and described.

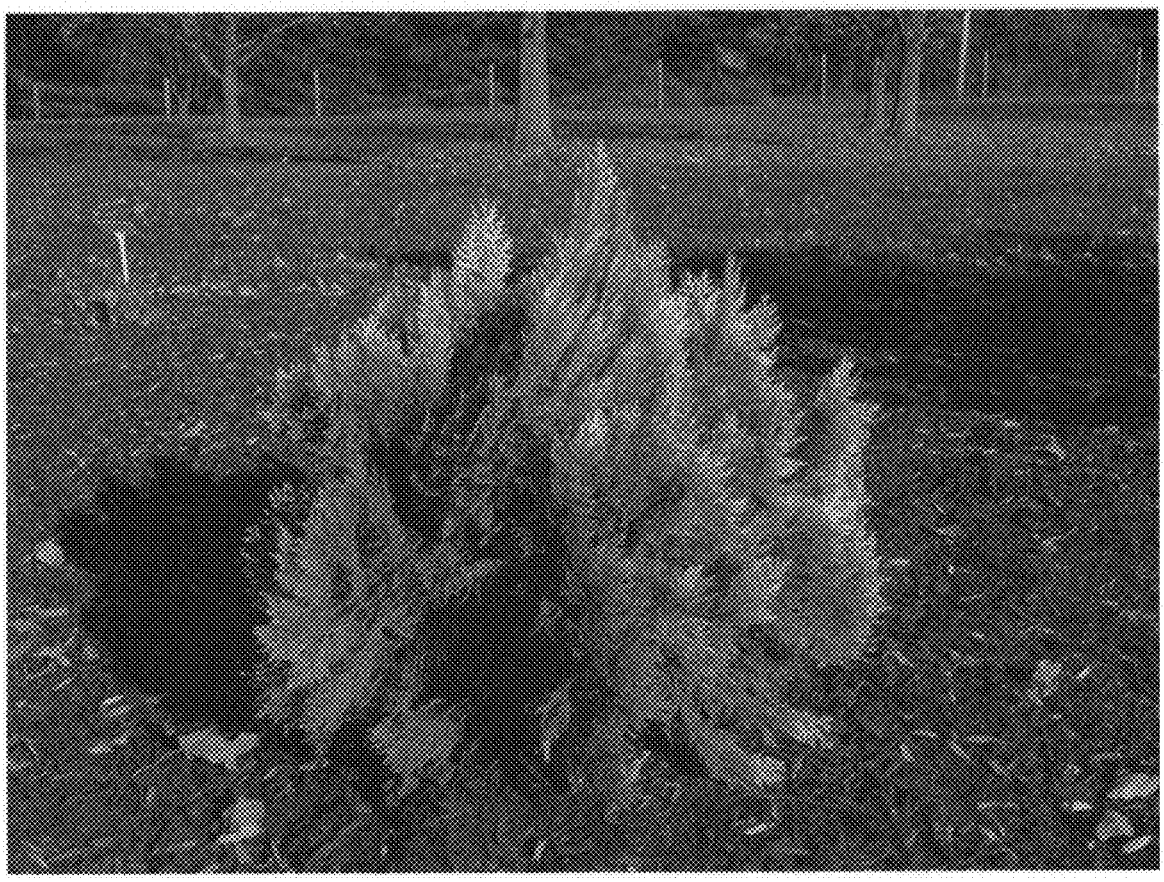

* * * * *